United States Patent
Baba et al.

(10) Patent No.: US 11,335,547 B2
(45) Date of Patent: May 17, 2022

(54) TOP DOWN ANALYSIS OF ANTIBODIES IN MASS SPECTROMETRY

(71) Applicant: DH TECHNOLOGIES DEVELOPMENT PTE. LTD., Singapore (SG)

(72) Inventors: Takashi Baba, Richmond Hill (CA); Pavel Ryumin, Toronto (CA); William M. Loyd, Sugar Land, TX (US)

(73) Assignee: DH Technologies Development Pte. Ltd., Singapore (SG)

( * ) Notice: Subject to any disclaimer, the term of this patent is extended or adjusted under 35 U.S.C. 154(b) by 32 days.

(21) Appl. No.: 17/041,324

(22) PCT Filed: Apr. 9, 2019

(86) PCT No.: PCT/IB2019/052906
§ 371 (c)(1),
(2) Date: Sep. 24, 2020

(87) PCT Pub. No.: WO2019/197983
PCT Pub. Date: Oct. 17, 2019

(65) Prior Publication Data
US 2021/0082678 A1    Mar. 18, 2021

Related U.S. Application Data

(60) Provisional application No. 62/655,540, filed on Apr. 10, 2018, provisional application No. 62/813,877, filed on Mar. 5, 2019.

(51) Int. Cl.
*H01J 49/40* (2006.01)
*G16B 40/10* (2019.01)
(Continued)

(52) U.S. Cl.
CPC ............ *H01J 49/40* (2013.01); *G01N 33/577* (2013.01); *G01N 33/6848* (2013.01);
(Continued)

(58) Field of Classification Search
CPC .. H01J 49/40; H01J 49/0045; G01N 33/6848; G01N 33/577; G16B 40/10; G16B 30/10
(Continued)

(56) References Cited

U.S. PATENT DOCUMENTS

2004/0077090 A1* 4/2004 Short ................. G01N 33/6818
506/1

FOREIGN PATENT DOCUMENTS

WO     2016-181299 A1    11/2016

OTHER PUBLICATIONS

International Search Report and Written Opinion for PCT/IB2019/052906, dated Aug. 16, 2019.
(Continued)

*Primary Examiner* — Kiet T Nguyen
(74) *Attorney, Agent, or Firm* — Kasha Law LLC; John R. Kasha; Kelly L. Kasha

(57) ABSTRACT

A separation device separates an unknown intact mAb or reduced mAb subunits of a known mAb class from a sample. An ion source device ionizes the mAb. A mass spectrometer fragments the ionized mAb using an ECD device and mass analyzes resulting product ions using a mass analyzer, producing one or more product ion spectra. Theoretical product ion peaks are calculated for one or more constant portions of the mAb class. The theoretical product ion peaks are removed from the one or more product ion spectra, producing one or more difference product ion spectra. De novo sequencing is applied to the one or more difference product ion spectra, producing one or more candidate sequences for one or more variable portions of the mAb. A
(Continued)

genome database is searched for matches to the one or more candidate sequences, producing one or more matched sequences for the one or more variable portions.

15 Claims, 12 Drawing Sheets

(51) Int. Cl.
  *G01N 33/68* (2006.01)
  *G01N 33/577* (2006.01)
  *H01J 49/00* (2006.01)
  *G16B 30/10* (2019.01)

(52) U.S. Cl.
  CPC .............. *G16B 30/10* (2019.02); *G16B 40/10* (2019.02); *H01J 49/0045* (2013.01)

(58) Field of Classification Search
  USPC .................................................. 250/281, 282
  See application file for complete search history.

(56) References Cited

OTHER PUBLICATIONS

Zhang, Zhongqi et al., "Characterization of variable regions of monoclonal antibodies by top-down mass spectrometry", Analytical Chemistry, 2007, vol. 79, No. 15, pp. 5723-5729.

Mao, Yuan et al., "Top-down structural analysis of an intact monoclonal antibody by electron capture dissociation-fourier transform ion cyclotron resonance-mass spectrometry", Analytical Chemistry, 2013, vol. 85, pp. 4239-4246.

Bondarenko, Pavel V. et al., "Mass measurement and top-down HPLC/MS analysis of intact monoclonal antibodies on a hybrid linear quadrupole ion trap-orbitrap mass spectrometer", Journal of the American Society for Mass Spectrometry, 2009, vol. 20, pp. 1415-1424.

Fornelli, Luca et al., "Middle-down analysis of monoclonal antibodies with electron transfer dissociation orbitrap Fourier transform mass spectrometry", Analytical Chemistry, 2014, vol. 86, pp. 3005-3012.

Tsybin, Yury O. et al., "Structural analysis of intact monoclonal antibodies by electron transfer dissociation mass spectrometry", Analytical Chemistry, 2011, vol. 83, pp. 8919-8927.

* cited by examiner

TOP DOWN ANALYSIS OF ANTIBODIES IN MASS SPECTROMETRY

RELATED APPLICATIONS

This application claims the benefit of U.S. Provisional Patent Application Ser. No. 62/655,540, filed on Apr. 10, 2018 and U.S. Provisional Patent Application Ser. No. 62/813,877, filed on Mar. 5, 2019, the content of both of which is incorporated by reference herein in its entirety.

INTRODUCTION

The teachings herein relate to mass spectrometry systems and methods for sequencing the variable portion of an unknown monoclonal antibody (mAb). More specifically, an electron capture dissociation (ECD) device is used to fragment an intact, digested, or reduced unknown mAb, producing product mass spectra. Theoretical product ion peaks calculated for constant portions of the mAb class are removed from the product mass spectra, producing difference product mass spectra. De novo sequencing is applied to the difference product ion spectra, producing candidate sequences for variable portions of the mAb. A genome database is searched, using a so called homology search, for matches to the one or more candidate sequences, producing matched sequences for the variable portions.

The systems and methods disclosed herein are also performed in conjunction with a processor, controller, microcontroller, or computer system, such as the computer system of FIG. 1.

Monoclonal Antibody Identification mAbs are proteins made by immune cells. These antibodies are monoclonal in that a certain antibody will only bind to a single binding site or paratope. Antibodies, in general, are used by an organism's immune system to mark foreign or diseased tissue for removal. Conversely, in autoimmune diseases, antibodies mistakenly attach to normal tissue causing that tissue also to be removed or damaged.

mAbs can be produced in large numbers in the laboratory for many different species. These laboratory produced mAbs have turned out to be highly effective and well-tolerated biologic drugs for humans. They have found use in fighting many different types of cancers and autoimmune diseases and are currently being tested in other diseases including Alzheimer's. According to Cotham et al., Anal. Chem., 2016, 88, 4004-4013 (hereinafter the "Cotham Paper"), upward of 300 therapeutic mAb candidates and their derivatives were in clinical drug development as late as 2016.

FIG. 2 is an exemplary diagram 200 of an IgG mAb. The mAb of FIG. 2 includes two identical long heavy chains 210 and two identical shorter light chains 220. Each of heavy chain 210 and light chain 220 includes constant and variable portions. The amino acid sequence of constant or fixed portions of mAbs does not have many variations. For example, the IgG class of mAb has four different subclasses. For each of these four different subclasses, the constant portions of the IgG mAb may vary. So there are just four different variations of the constant portions for the entire IgG class.

In contrast, the variable portions of mAbs can vary significantly and give mAbs their unique ability to find and attach to billions of different types of foreign or diseased tissue. These variable portions include the binding sites or paratopes of mAbs. Although the human genome includes less than 20,000 genes, the body is able to produce antibodies with billions of different variable portions, or, more specifically, billions of different paratopes. Dr. Susumu Tonegawa received the Nobel Prize for Physiology or Medicine in 1987 for discovering that different portions of genes can be selected and combined to produce these billions of different variable portions.

Each heavy chain 210 of the IgG mAb in FIG. 2 includes constant portions 211, 212, and 213 and one variable portion 214. Each light chain 220 includes one constant portion 221 and one variable portion 222. The variable portion 214 of each heavy chain 210 includes binding site 215, and the variable portion 222 of each light chain 220 includes binding site 223.

The increased use of therapeutic mAbs has increased the need to experimentally identify their amino acid sequence. Mass spectrometry/mass spectrometry (MS/MS) is often used to determine the amino acid sequence of peptides and proteins. Recently, top-down and middle-down MS/MS methods have been used to identify the sequence of known therapeutic mAbs.

For example, Fornelli et al., Mol Cell Proteomics, 2012 December;11(12):1758-67 (hereinafter the "First Fornelli Paper") proposed a top-down MS/MS approach to sequence intact mAbs. This approach was chosen in order to characterize mAbs and their post-translational modifications (PTMs).

FIG. 3 is a schematic diagram 300 showing the top-down MS/MS approach used in the First Fornelli Paper. In step 310 of FIG. 3, a sample is prepared of many copies of a known intact mAb in solution. In step 320, liquid chromatography (LC) is performed on the solution to separate and desalt the mAb.

In step 330, MS/MS is performed on the separated mAb. For example, the separated mAb is ionized using ion source device 331, and the mAb precursor ions are fragmented using electron transfer dissociation (ETD) in linear ion trap (LTQ) 332. The First Fornelli Paper describes that electron capture dissociation (ECD) and ETD are ion activation techniques that allow polypeptide fragmentation with reduced PTM loses. Finally, the precursor and product ions are detected using orbitrap Fourier Transform mass spectrometer (FT-MS) 333, producing a plurality of product ion spectra 334.

In step 340, analysis of fragmentation patterns in plurality of product ion spectra 334 is performed using top-down MS/MS analysis software. Searches are performed against a custom sequence database 341 incorporating the known sequences of both the light and heavy chains of the known mAb. From these searches, the First Fornelli Paper reported a matching sequence 342 with about 33% coverage of the intact known mAb.

Fornelli et al., Anal. Chem., 2014, 86, 3005-3012 (hereinafter the "Second Fornelli Paper") proposed a middle-down MS/MS approach to sequence mAbs. The Second Fornelli Paper describes that the success of mAbs as therapeutics has required that these mAbs be well characterized structurally to ensure their safety, efficiency, batch-to-batch consistency, and stability. As a result, the 33% sequence coverage of the method of the First Fornelli Paper had to be improved. To do this, the Second Fornelli Paper proposed chemically reducing a mAb into large fragments or subunits before MS/MS analysis. This use of reduced mAb subunits is referred to as middle-down MS/MS analysis.

FIG. 4 is a schematic diagram 400 showing the middle-down MS/MS approach used in the Second Fornelli Paper. In step 410 of FIG. 4, a sample is prepared of many copies of a known intact mAb in solution. In step 420, however, immunoglobulin G-degrading enzyme of Streptococcus pyogenes (IdeS) digestion of the mAb and reduction of the digested mAb using a disulfide bond reducing agent 421 are performed before LC. In step 430, LC is performed on mAb subunits to separate and desalt the mAb subunits.

In step 440, MS/MS is performed on the separated mAb subunits. For example, the separated mAb subunits are ionized using ion source device 441, and the mAb subunit precursor ions are fragmented using electron transfer dissociation (ETD) in linear ion trap (LTQ) 442. Finally, the precursor and product ions are detected using orbitrap FT-MS 443, producing a plurality of product ion spectra 444.

In step 450, analysis of fragmentation patterns in plurality of product ion spectra 444 is performed using MS analysis software. Searches are performed against a database 451 incorporating the known sequences of both the light and heavy chains of the known mAb. From these searches, the Second Fornelli Paper reported a matching sequence 452 with about 50% coverage of the intact known mAb.

Like the Second Fornelli Paper, the Cotham Paper describes that the therapeutic efficacy of mAbs is regulated by structural integrity with regard to the primary sequence and the presence and abundance of PTMs. As a result, the Cotham Paper finds that characterization of the antibody primary sequence in addition to PTM identification and site localization is critical to ensure mAb safety and efficacy. The Cotham Paper reviews the methods of the First Fornelli Paper and the Second Fornelli Paper and proposes a middle-down approach, like the Second Fornelli Paper, but with the ETD fragmentation replaced by 193 nm ultraviolet photodissociation (UVPD).

FIG. 5 is a schematic diagram 500 showing the middle-down MS/MS approach used in the Cotham Paper. In step 510 of FIG. 5, a sample is prepared of many copies of a known intact mAb in solution. In step 520, IdeS digestion of the mAb and reduction and denaturation of the digested mAb are performed before LC. In step 530, LC is performed on the mAb subunits.

In step 540, MS/MS is performed on the separated mAb subunits. For example, the separated mAb subunits are ionized using ion source device 541, and the mAb subunit precursor ions are fragmented using UVPD in higher-energy collisional dissociation (HCD) cell 542. Finally, the precursor and product ions are detected using orbitrap FT-MS 543, producing a plurality of product ion spectra 544.

In step 550, plurality of product ion spectra 544 is analyzed using MS analysis software. Using the method of FIG. 5, the Cotham Paper reported approximately 60% overall sequence coverage of the known mAb.

In step 550, analysis of fragmentation patterns of a single spectrum 545 averaged from plurality of product ion spectra 544 is performed using MS analysis software. Searches are performed against a database 551 incorporating the known sequences of both the light and heavy chains of the known mAb. From these searches, the Cotham Paper reported a matching sequence 552 with about 60% coverage of the intact known mAb.

The First Fornelli Paper, the Second Fornelli Paper, and the Cotham Paper are all directed to identifying a known mAb in a sample solution. As described by the Second Fornelli Paper, these methods can be used in mAb drug development to show that the manufactured mAbs have similar physicochemical characteristics, functional properties, and clinical efficiency to those of the innovator product.

The methods of the First Fornelli Paper, the Second Fornelli Paper, and the Cotham Paper are not directed to sequencing unknown mAbs. In other words, these methods are not directed to mAb drug discovery. Determining the sequence of an unknown mAb is a much more difficult problem than identifying or confirming the sequence of a known mAb in a solution. It is a much more difficult problem, because, as described above, the variable portion of a mAb can have billions of different possible sequences.

As a result, there is a need for systems and methods to determine the sequence of an unknown mAb. More specifically, there is a need for systems and methods to determine the sequence of the variable portion of an unknown mAb.

Mass Spectrometry Background

Mass spectrometry (MS) is an analytical technique for detection and quantitation of chemical compounds based on the analysis of m/z values of ions formed from those compounds. MS involves ionization of one or more compounds of interest from a sample, producing precursor ions, and mass analysis of the precursor ions.

Tandem mass spectrometry or mass spectrometry/mass spectrometry (MS/MS) involves ionization of one or more compounds of interest from a sample, selection of one or more precursor ions of the one or more compounds, fragmentation of the one or more precursor ions into product ions, and mass analysis of the product ions.

Both MS and MS/MS can provide qualitative and quantitative information. The measured precursor or product ion spectrum can be used to identify a molecule of interest. The intensities of precursor ions and product ions can also be used to quantitate the amount of the compound present in a sample.

Fragmentation Techniques Background

Electron-based dissociation (ExD), ultraviolet photodissociation (UVPD), infrared photodissociation (IRMPD) and collision-induced dissociation (CID) are often used as fragmentation techniques for tandem mass spectrometry (MS/MS). ExD can include, but is not limited to, electron capture dissociation (ECD) or electron transfer dissociation (ETD). CID is the most conventional technique for dissociation in tandem mass spectrometers.

As described above, in top-down and middle-down proteomics, an intact or digested protein is ionized and subjected to tandem mass spectrometry. ECD, for example, is a dissociation technique that dissociates peptide and protein backbones preferentially. As a result, this technique is an ideal tool to analyze peptide or protein sequences using a top-down and middle-down proteomics approach.

SUMMARY

A system, method, and computer program product are disclosed for sequencing one or more variable portions of an unknown mAb. The system includes a genome database, a separation device, an ion source device, a mass spectrometer with one or more dissociation devices, and a processor.

The processor instructs the separation device to separate an unknown intact mAb or reduced mAb subunits of a known mAb class from a sample. The processor instructs the ion source device to ionize the unknown intact mAb or reduced mAb subunits. The mass spectrometer includes a dissociation device and a mass analyzer. The dissociation device is preferably an ECD device. The processor instructs the mass spectrometer to fragment the ionized unknown intact mAb or reduced mAb subunits using the dissociation device and to mass analyze resulting product ions using the mass analyzer, producing one or more product ion spectra.

The processor calculates theoretical product ion peaks for one or more constant portions of the known mAb class. The processor removes the calculated theoretical product ion peaks from the one or more product ion spectra, producing one or more difference product ion spectra. The processor applies de novo sequencing to the one or more difference product ion spectra, producing one or more candidate sequences for one or more variable portions of the unknown intact mAb or reduced mAb subunits. The processor searches (homology search) the genome database for matches to the one or more candidate sequences, producing one or more matched sequences for the one or more variable portions.

These and other features of the applicant's teachings are set forth herein.

BRIEF DESCRIPTION OF THE DRAWINGS

The skilled artisan will understand that the drawings, described below, are for illustration purposes only. The drawings are not intended to limit the scope of the present teachings in any way.

Figure 1:
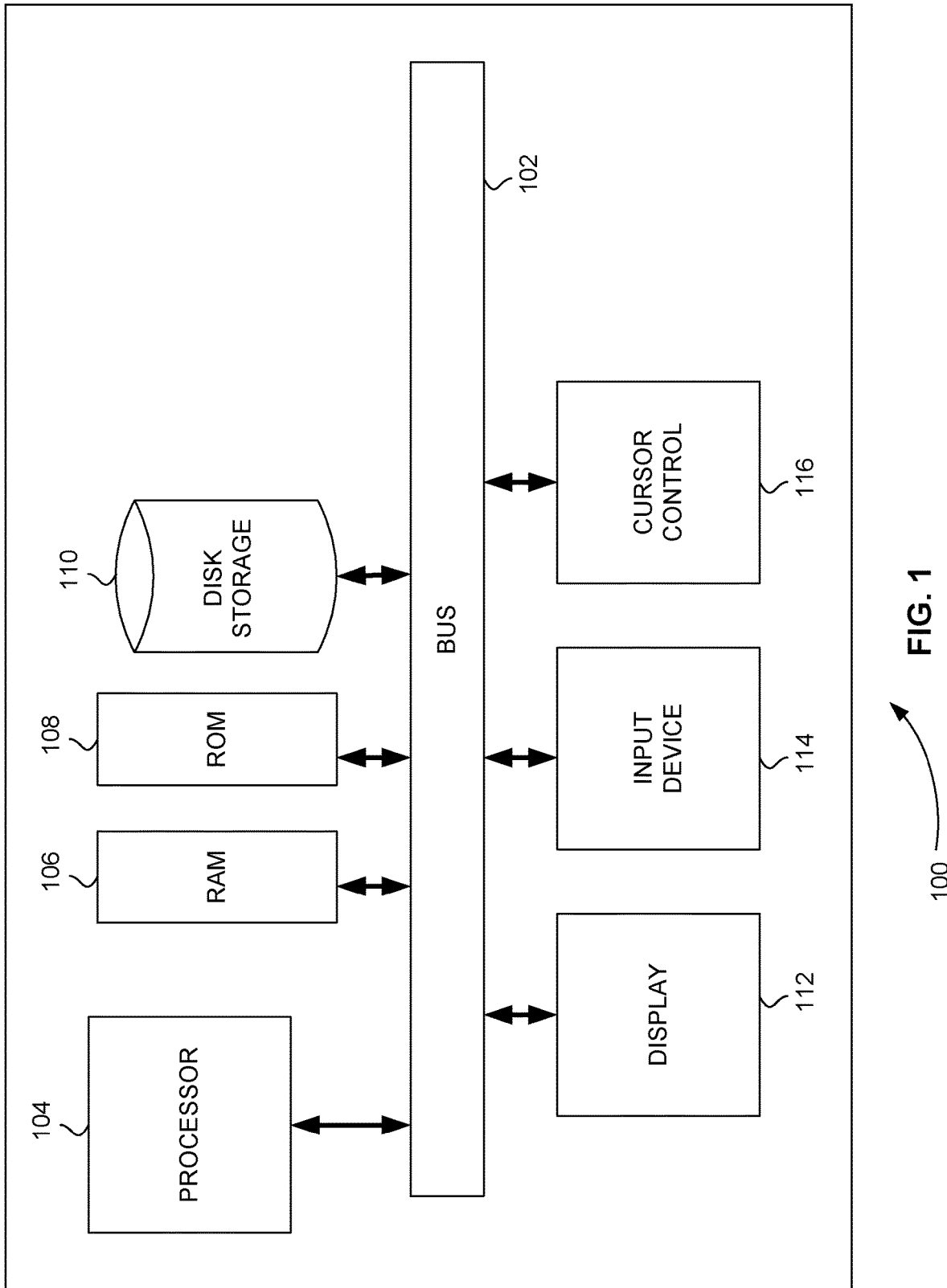
FIG. 1 is a block diagram that illustrates a computer system, upon which embodiments of the present teachings may be implemented.
Figure 2:
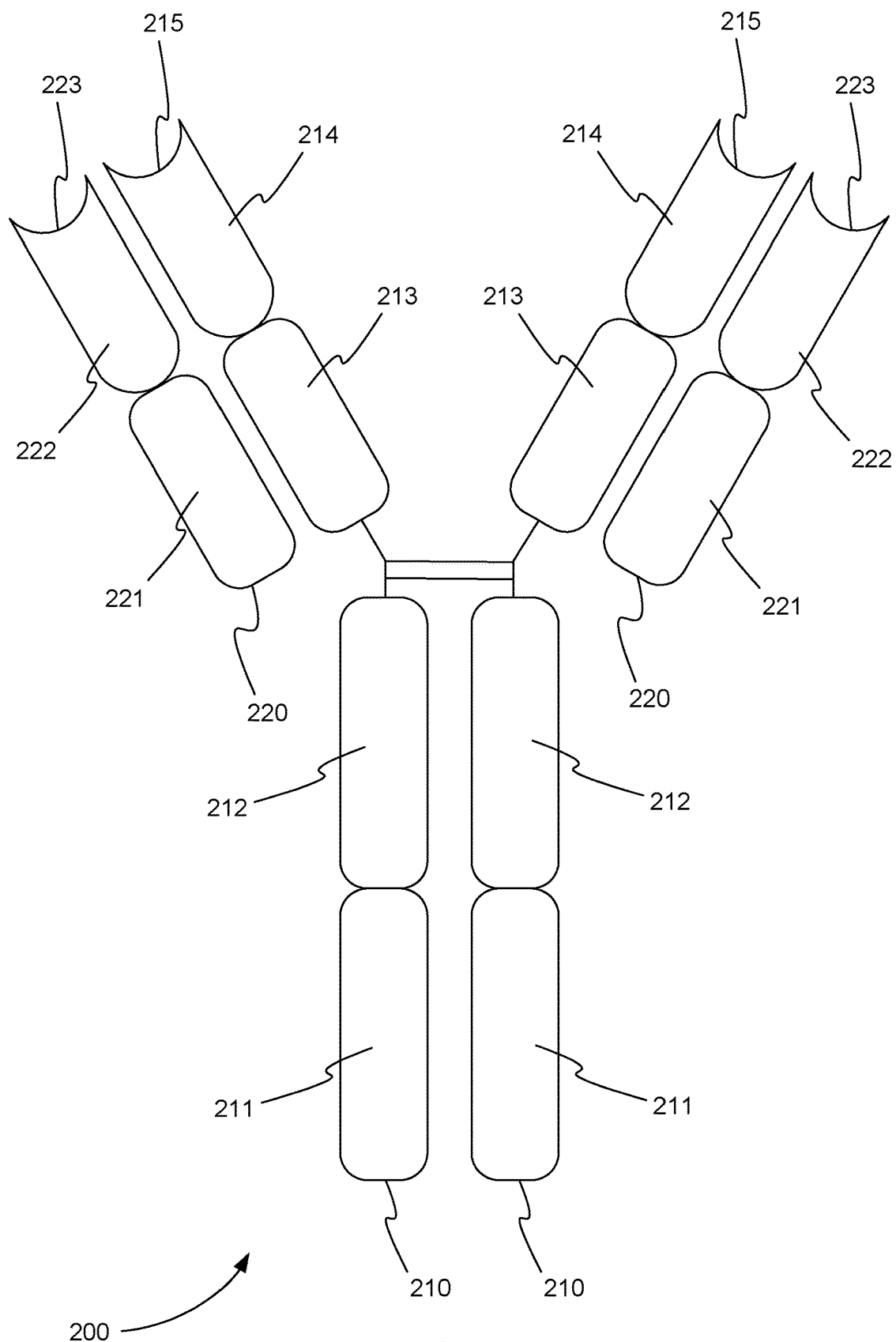
FIG. 2 is an exemplary diagram of an IgG monoclonal antibody (mAb).
Figure 3:
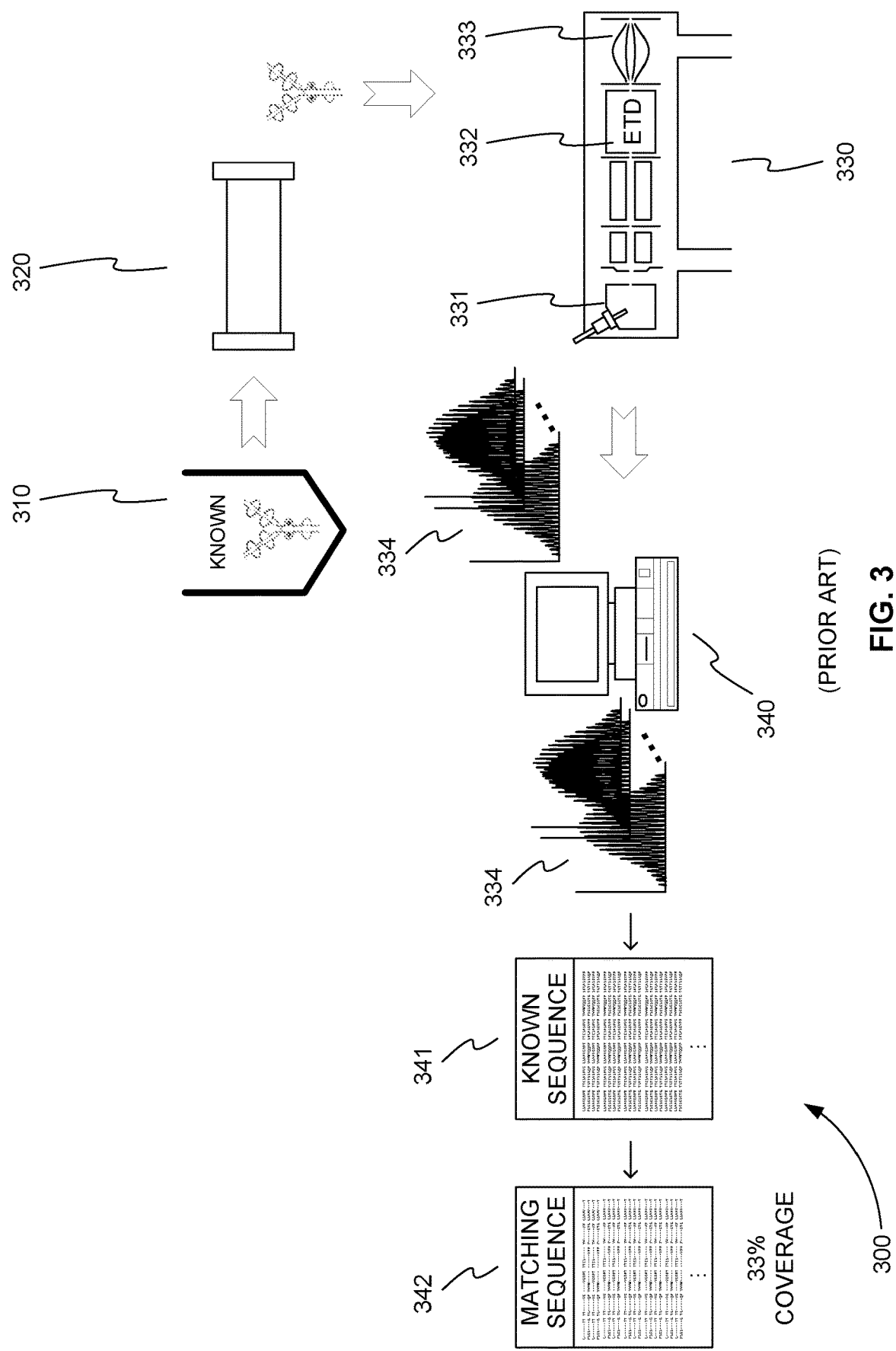
FIG. 3 is a schematic diagram showing the top-down MS/MS approach used in the First Fornelli Paper.
Figure 4:
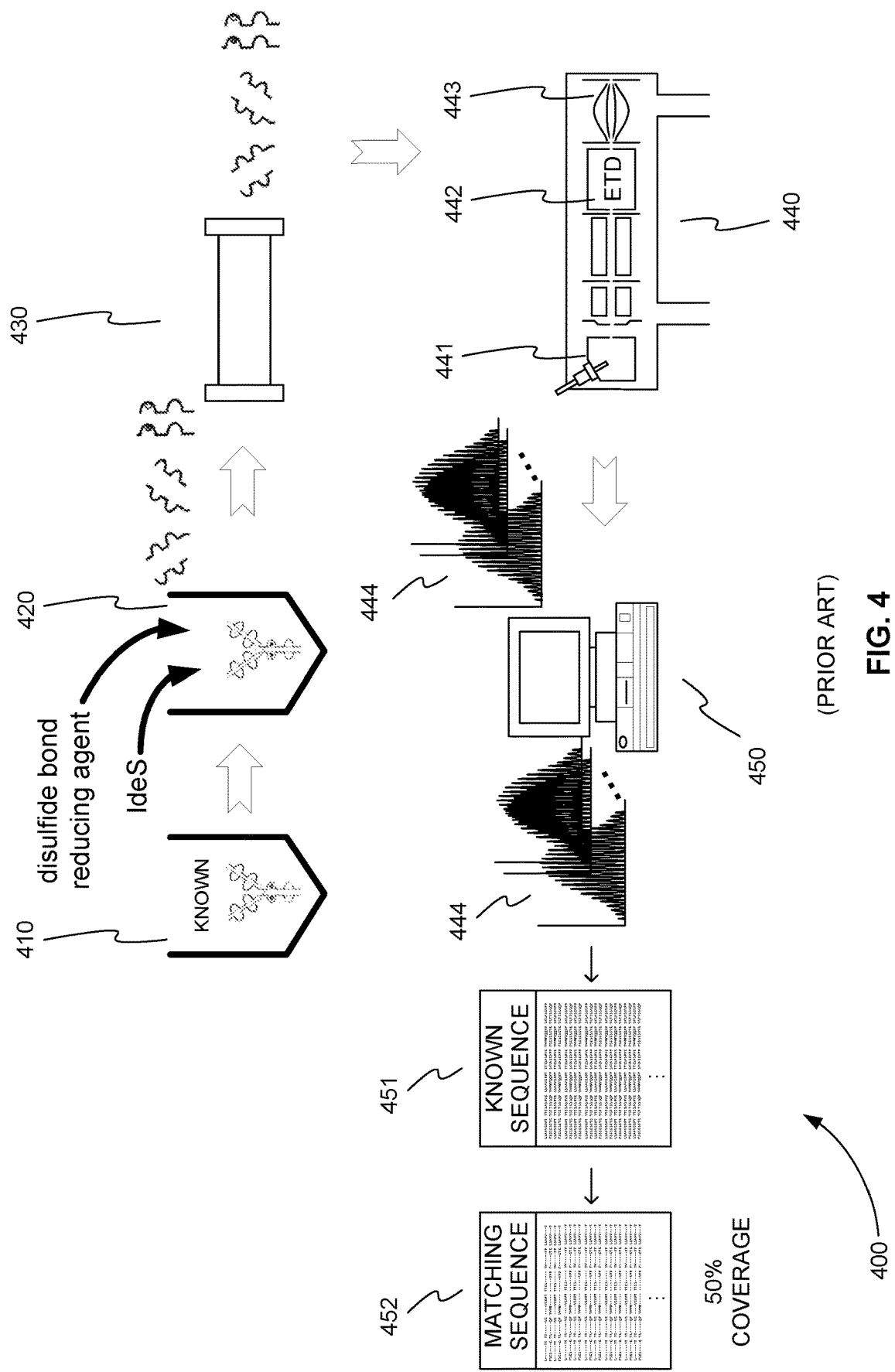
FIG. 4 is a schematic diagram showing the middle-down MS/MS approach used in the Second Fornelli Paper.
Figure 5:
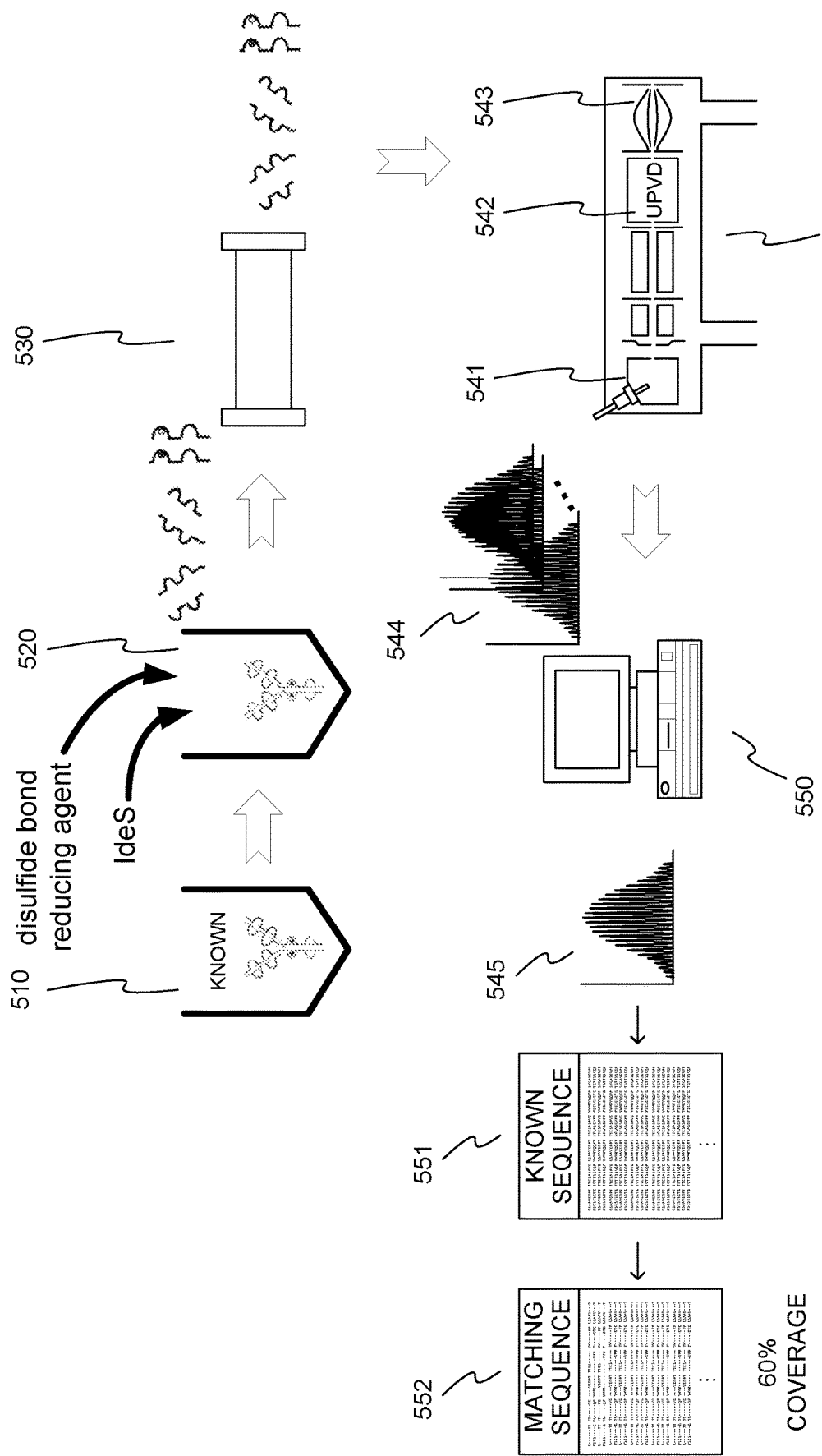
FIG. 5 is a schematic diagram showing the middle-down MS/MS approach used in the Cotham Paper.

Before one or more embodiments of the present teachings are described in detail, one skilled in the art will appreciate that the present teachings are not limited in their application to the details of construction, the arrangements of components, and the arrangement of steps set forth in the following detailed description or illustrated in the drawings. Also, it is to be understood that the phraseology and terminology used herein is for the purpose of description and should not be regarded as limiting.

DESCRIPTION OF VARIOUS EMBODIMENTS

Computer-Implemented System

FIG. 1 is a block diagram that illustrates a computer system 100, upon which embodiments of the present teachings may be implemented. Computer system 100 includes a bus 102 or other communication mechanism for communicating information, and a processor 104 coupled with bus 102 for processing information. Computer system 100 also includes a memory 106, which can be a random access memory (RAM) or other dynamic storage device, coupled to bus 102 for storing instructions to be executed by processor 104. Memory 106 also may be used for storing temporary variables or other intermediate information during execution of instructions to be executed by processor 104. Computer system 100 further includes a read only memory (ROM) 108 or other static storage device coupled to bus 102 for storing static information and instructions for processor 104. A storage device 110, such as a magnetic disk or optical disk, is provided and coupled to bus 102 for storing information and instructions.

Computer system 100 may be coupled via bus 102 to a display 112, such as a cathode ray tube (CRT) or liquid crystal display (LCD), for displaying information to a computer user. An input device 114, including alphanumeric and other keys, is coupled to bus 102 for communicating information and command selections to processor 104. Another type of user input device is cursor control 116, such as a mouse, a trackball or cursor direction keys for communicating direction information and command selections to processor 104 and for controlling cursor movement on display 112. This input device typically has two degrees of freedom in two axes, a first axis (i.e., x) and a second axis (i.e., y), that allows the device to specify positions in a plane.

A computer system 100 can perform the present teachings Consistent with certain implementations of the present teachings, results are provided by computer system 100 in response to processor 104 executing one or more sequences of one or more instructions contained in memory 106. Such instructions may be read into memory 106 from another computer-readable medium, such as storage device 110. Execution of the sequences of instructions contained in memory 106 causes processor 104 to perform the process described herein. Alternatively, hard-wired circuitry may be used in place of or in combination with software instructions to implement the present teachings. Thus implementations of the present teachings are not limited to any specific combination of hardware circuitry and software.

In various embodiments, computer system 100 can be connected to one or more other computer systems, like computer system 100, across a network to form a networked system. The network can include a private network or a public network such as the Internet. In the networked system, one or more computer systems can store and serve the data to other computer systems. The one or more computer systems that store and serve the data can be referred to as servers or the cloud, in a cloud computing scenario. The one or more computer systems can include one or more web servers, for example. The other computer systems that send and receive data to and from the servers or the cloud can be referred to as client or cloud devices, for example.

The term "computer-readable medium" as used herein refers to any media that participates in providing instructions to processor 104 for execution. Such a medium may take many forms, including but not limited to, non-volatile media, volatile media, and transmission media. Non-volatile media includes, for example, optical or magnetic disks, such as storage device 110. Volatile media includes dynamic memory, such as memory 106. Transmission media includes coaxial cables, copper wire, and fiber optics, including the wires that comprise bus 102.

Common forms of computer-readable media or computer program products include, for example, a floppy disk, a flexible disk, hard disk, magnetic tape, or any other magnetic medium, a CD-ROM, digital video disc (DVD), a Blu-ray Disc, any other optical medium, a thumb drive, a memory card, a RAM, PROM, and EPROM, a FLASH-EPROM, any other memory chip or cartridge, or any other tangible medium from which a computer can read.

Various forms of computer readable media may be involved in carrying one or more sequences of one or more instructions to processor 104 for execution. For example, the instructions may initially be carried on the magnetic disk of a remote computer. The remote computer can load the instructions into its dynamic memory and send the instructions over a telephone line using a modem. A modem local to computer system 100 can receive the data on the telephone line and use an infra-red transmitter to convert the data to an infra-red signal. An infra-red detector coupled to bus 102 can receive the data carried in the infra-red signal and place the data on bus 102. Bus 102 carries the data to memory 106, from which processor 104 retrieves and executes the instructions. The instructions received by memory 106 may optionally be stored on storage device 110 either before or after execution by processor 104.

In accordance with various embodiments, instructions configured to be executed by a processor to perform a method are stored on a computer-readable medium. The computer-readable medium can be a device that stores digital information. For example, a computer-readable medium includes a compact disc read-only memory (CD-ROM) as is known in the art for storing software. The computer-readable medium is accessed by a processor suitable for executing instructions configured to be executed.

The following descriptions of various implementations of the present teachings have been presented for purposes of illustration and description. It is not exhaustive and does not limit the present teachings to the precise form disclosed. Modifications and variations are possible in light of the above teachings or may be acquired from practicing of the present teachings. Additionally, the described implementation includes software, but the present teachings may be implemented as a combination of hardware and software or in hardware alone. The present teachings may be implemented with both object-oriented and non-object-oriented programming systems.

Mabs Variable Portion Determination

As described above, top-down and middle-down analysis of monoclonal antibodies (mAbs) has only be demonstrated when the amino acid sequence of a mAb is known. Determining the sequence of an unknown mAb is a much more difficult problem than identifying or confirming the sequence of a known mAb. It is a much more difficult problem, because, as described above, the variable portion of a mAb can have billions of different possible sequences.

As a result, there is a need for systems and methods to determine the sequence of an unknown mAb. More specifically, there is a need for systems and methods to determine the sequence of the variable portion of an unknown mAbs.

In various embodiments, systems and methods are provided to sequence the variable portion of an unknown mAb. Top-down or middle-down LC-MS/MS is used. Top-down LC-MS/MS is applied to an intact mAb. Middle-down LC-MS/MS is applied to reduced mAb subunits.

Theoretical product ion peaks for one or more constant portions of the known mAb class are calculated. These calculated theoretical product ion peaks are removed or subtracted from the one or more product ion spectra produced by the top-down or middle-down LC-MS/MS. De novo sequencing is applied to the one or more difference product ion spectra, producing one or more candidate sequences for one or more variable portions of the unknown intact mAb or reduced mAb subunits. Finally, a genome database is searched (homology search) for matches to the one or more candidate sequences, producing one or more matched sequences for the one or more variable portions of the unknown mAb. In various embodiments, traditional top-down or middle-down MS/MS is performed again to validate the one or more matched sequences.

System for Sequencing Variable Portion of unknown mAb

Figure 6:
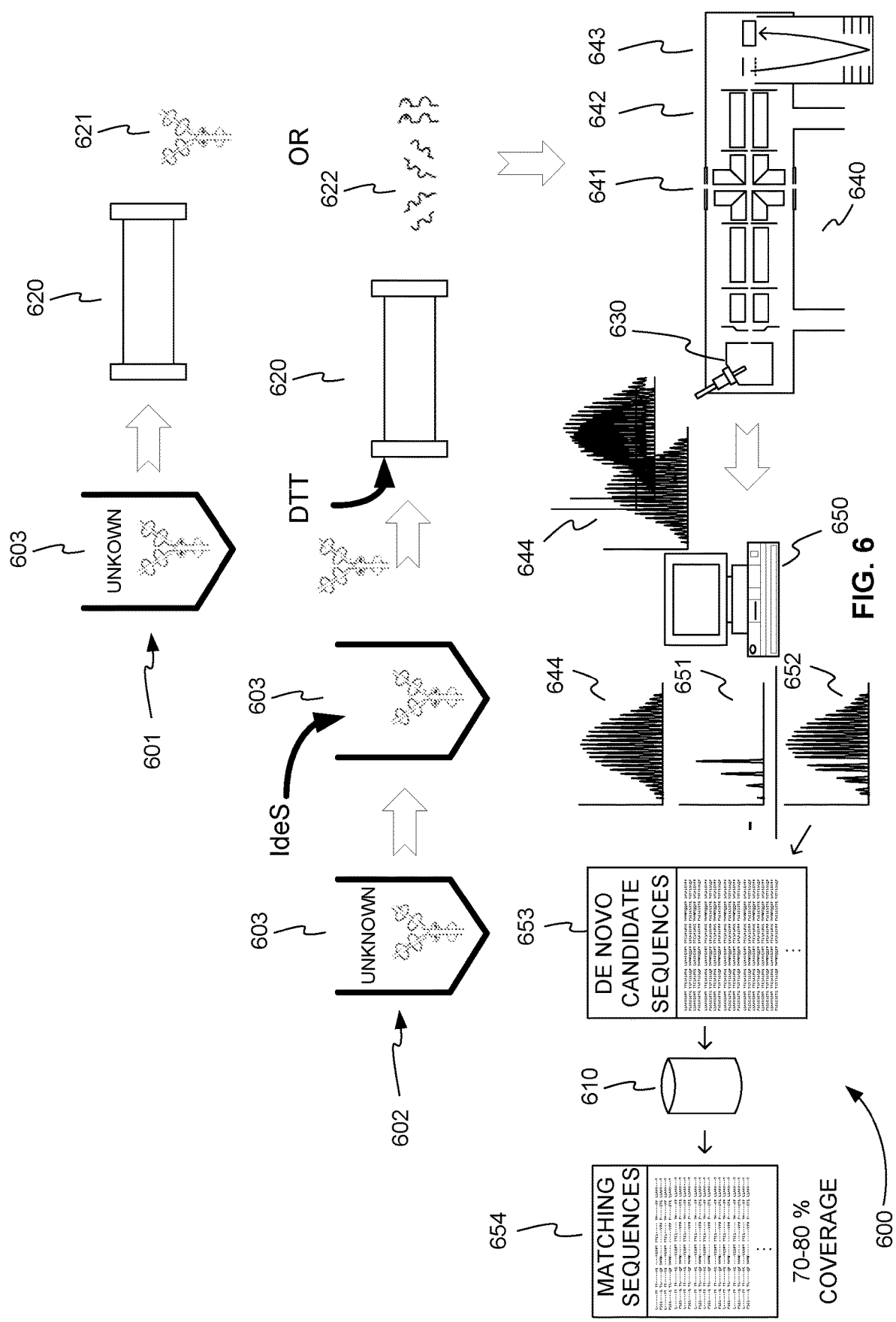
FIG. 6 is an exemplary schematic diagram showing a system for sequencing one or more variable portions of an unknown mAb, in accordance with various embodiments.

FIG. 6 is an exemplary schematic diagram 600 showing a system for sequencing one or more variable portions of an unknown mAb, in accordance with various embodiments. The system of FIG. 6 includes genome database 610, separation device 620, ion source device 630, mass spectrometer 640, and processor 650.

Processor 650 instructs separation device 620 to separate an unknown intact mAb or reduced mAb subunits of a known mAb class from a sample. In various embodiments, processor 650 is used to control or provide instructions to separation device 620, ion source device 630, and mass spectrometer 640, to search genome database 610, and to analyze data collected. Processor 650 controls or provides instructions by, for example, controlling one or more voltage, current, or pressure sources (not shown). Processor 650 can be a separate device as shown in FIG. 6 or can be a processor or controller of one or more devices of mass spectrometer 640. Processor 650 can be, but is not limited to, a controller, a computer, a microprocessor, the computer system of FIG. 1, or any device capable of sending and receiving control signals and data and analyzing data.

In various embodiments, processor 650 instructs separation device 620 to separate an intact unknown mAb in a top-down method as shown in step 601. An intact unknown mAb in solution 603 is supplied to separation device 620 in this top-down method, and intact unknown mAb 621 is desalted and separated by separation device 620.

In various alternative embodiments, processor 650 instructs separation device 620 to separate a digested unknown mAb in a middle-down method as shown in step 602. An intact unknown mAb in digest solution 603 is digested by applying IdeS to solution 603. The digested unknown mAb is then supplied to separation device 620 in this middle-down method, and digested unknown mAb 622 is desalted by separation device 620.

In various embodiments, dithiothreitol (DTT) is used to reduce the digested unknown mAb. For example, DTT is injected into separation device 620 for online reduction. Separation device 620 is separating the reduced IdeS digest of the unknown mAb.

Separation device 620 can be, but is not limited to, a liquid chromatography (LC) device or a capillary electrophoresis device. In a preferred embodiment, separation device 620 is an LC column that separates and desalts the unknown intact mAb or reduced mAb subunits over time.

Processor 650 instructs ion source device 630 to ionize unknown intact mAb 621 or reduced mAb subunits 622. Ion source device 630 can be an electrospray ion source (ESI) device. Ion source device 630 is shown as part of mass spectrometer 640 in FIG. 6.

Mass spectrometer 640 includes, among other devices, dissociation device 641 and mass analyzer 643. Processor 650 instructs mass spectrometer 640 to fragment the ionized unknown intact mAb or reduced mAb subunits using dissociation device 641 and mass analyze resulting product ions using mass analyzer 643, producing one or more product ion spectra 644. Mass analyzer 643 can include, but is not limited to, a time-of-flight (TOF) mass analyzer, a quadrupole, an ion trap, a linear ion trap, an orbitrap, a magnetic sector mass analyzer, a hybrid quadrupole time-of-flight (Q-TOF) mass analyzer, or a Fourier transform ion cyclotron resonance mass analyzer. In a preferred embodiment, mass analyzer 643 is a TOF mass analyzer.

Dissociation device 641 fragments the ionized unknown intact mAb or reduced mAb subunits using ExD, IRMPD, CID, or UVPD, for example. In a preferred embodiment, dissociation device 641 is an ECD device.

Figure 7:
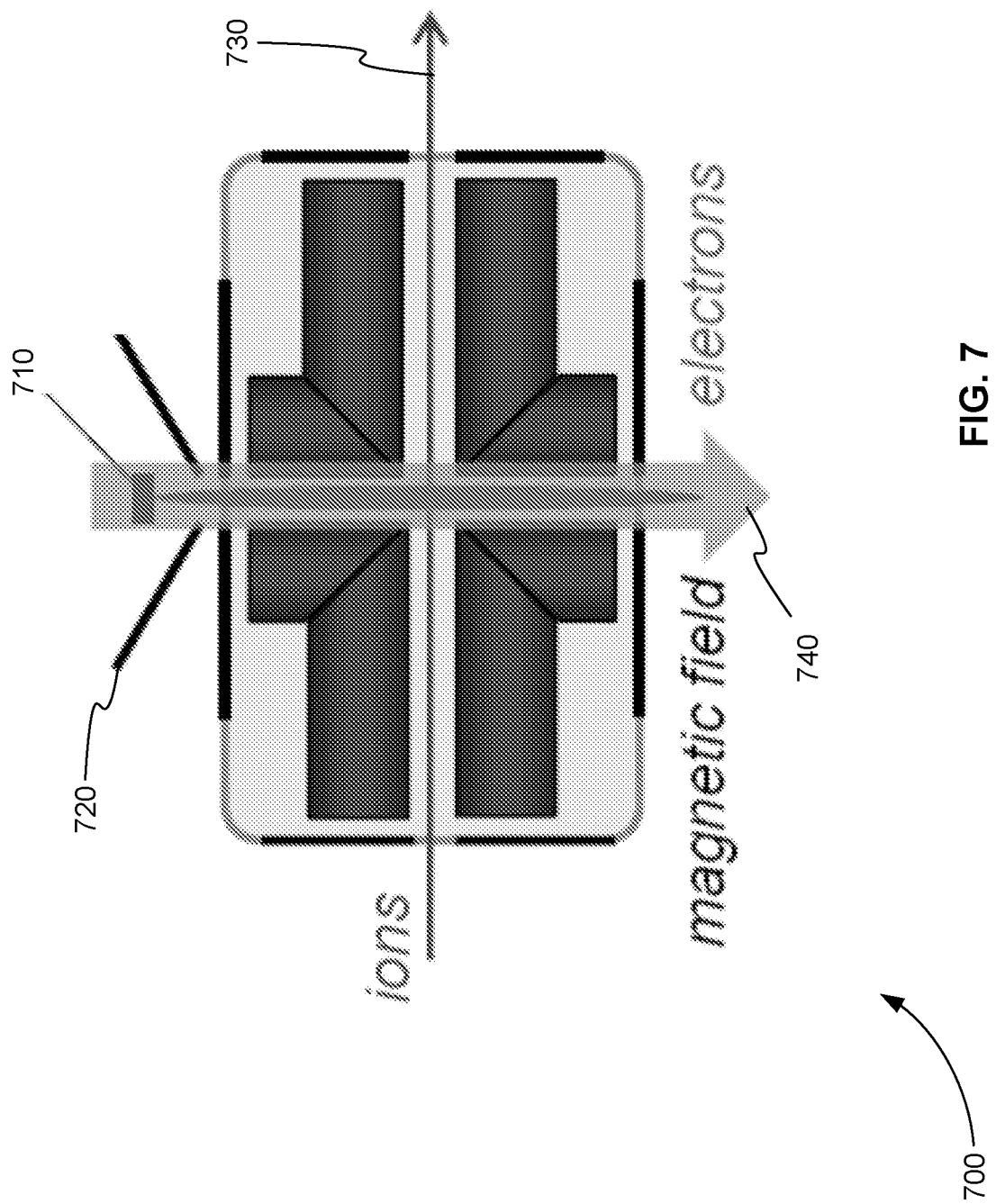
FIG. 7 is a schematic diagram of an electron capture dissociation (ECD) device, in accordance with various embodiments.

FIG. 7 is a schematic diagram 700 of an ECD device, in accordance with various embodiments. The ECD device includes electron emitter or filament 710 and electron gate 720. Electrons are emitted perpendicular to the flow of ions 730 and parallel to the direction of magnetic field 740.

Returning to FIG. 6, mass spectrometers that include a dissociation device, typically include another dissociation device, like Q2 dissociation device 642 for CID. Q2 dissociation device 642 is used to fragment compounds other than proteins or peptides, for example. During the analysis of proteins or peptides, Q2 dissociation device 642 acts as an ion guide and simply transmits product ions from dissociation device 641 to mass analyzer 643.

Figure 8:
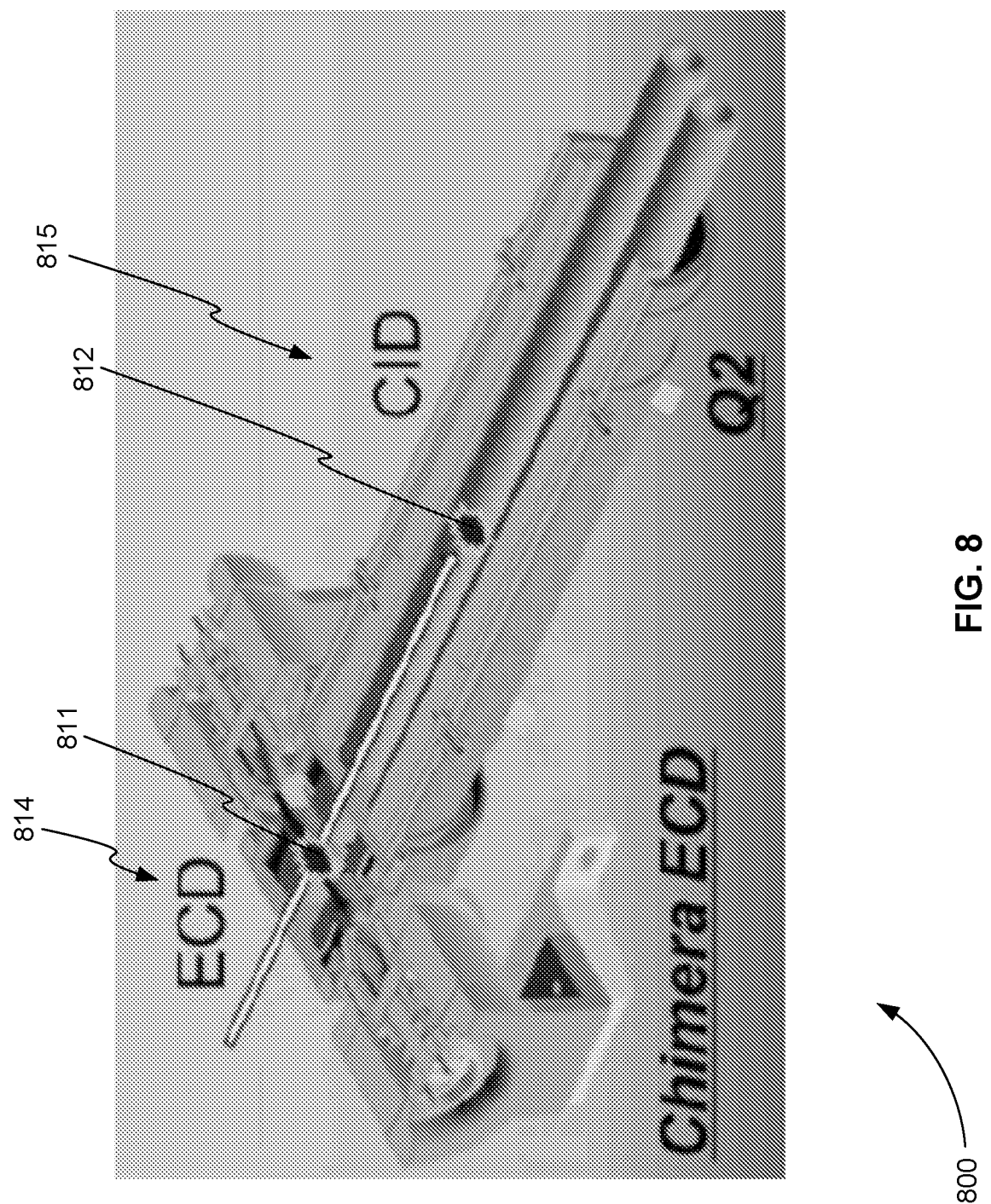
FIG. 8 is a cutaway three-dimensional perspective view of an ECD device and a collision-induced dissociation (CID) collision cell, in accordance with various embodiments.

FIG. 8 is a cutaway three-dimensional perspective view 800 of an ECD device and a CID collision cell, in accordance with various embodiments. FIG. 8 shows that fragmentation of ions selectively can be performed at location 811 in ECD device 814 or at location 812 in CID collision cell 815.

Returning to FIG. 6, in various embodiments, processor 650 instructs mass spectrometer 640 to use an electron energy between 0 and 3 eV to fragment the ionized unknown intact mAb or reduced mAb subunits using ECD dissociation device 641. Mass spectrometer 640 simultaneously injects electrons and ions of the unknown intact mAb or reduced mAb subunits into ECD dissociation device 641.

In various embodiments, ECD dissociation device 641 is a quadrupole, hexapole, or octupole dissociation device.

Processor 650 calculates theoretical product ion peaks 651 for one or more constant portions of the known mAb class. mAb classes can include, but are not limited to, IgG, IgE, IgD, IgM, and IgA.

Processor 650 removes or subtracts calculated theoretical product ion peaks 651 from one or more product ion spectra 644, producing one or more difference product ion spectra 652.

Processor 650 applies de novo sequencing to one or more difference product ion spectra 652, producing one or more candidate sequences 653 for one or more variable portions of the unknown intact mAb or reduced mAb subunits. Processor 650 searches (homology search) genome database 610 for matches to one or more candidate sequences 653, producing one or more matched sequences 654 for the one or more variable portions.

In de novo sequencing, one or more amino acid sequences are assigned to the product ions in a product ion spectrum, for example. Note that de novo sequencing is different from the database search that is performed by the First Fornelli Paper, the Second Fornelli Paper, and the Cotham Paper to find a sequence. There is no database search in order to determine the candidate sequence in de novo sequencing.

In various embodiments, processor 650 removes calculated theoretical product ion peaks 651 by removing theoretical product ion peaks of C-terminal product ions. Processor 650 applies de novo sequencing to remaining N-terminal product ions of one or more difference product ion spectra 652 to produce one or more candidate sequences 653.

As described below, the system of FIG. 6 was found to produce a 70-80% sequence coverage of the unknown mAb. In various embodiments, processor 650 determines the sequence coverage and confirms the one or matched sequences by further comparing the one or matched sequences to the one or more product ion spectra of the unknown intact mAb or reduced mAb subunits.

In various embodiments, processor 650 calculates a peak list from the one or more product ion spectra 644. For example, processor 650 can calculate the peak list from one or more product ion spectra 644 that are converted to singly charged product ion peaks. Processor 650 then removes the calculated theoretical product ion peaks 651 from the one or more product ion spectra by removing theoretical product ion peaks 651 from the peak list, producing a difference peak list. Processor 650 applies de novo sequencing to one or more difference product ion spectra 652 by applying de novo sequencing to the difference peak list.

Figure 9:
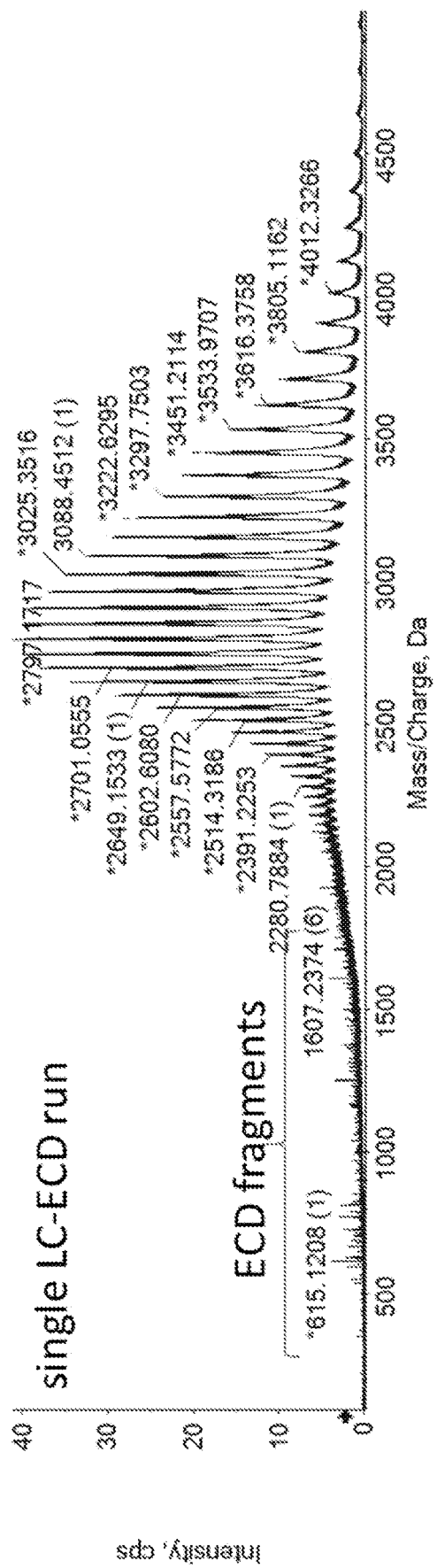
FIG. 9 is an exemplary product ion spectrum produced by fragmenting a non-reduced intact mAb using ECD dissociation, in accordance with various embodiments.

FIG. 9 is an exemplary product ion spectrum 900 produced by fragmenting a non-reduced intact mAb using ECD dissociation, in accordance with various embodiments. In ECD product ion spectrum 900, singly charged product ions appear between about 500 and 1500 m/z. Multiply charged precursor ions appear between about 2100 and 4500 m/z.

Figure 10:
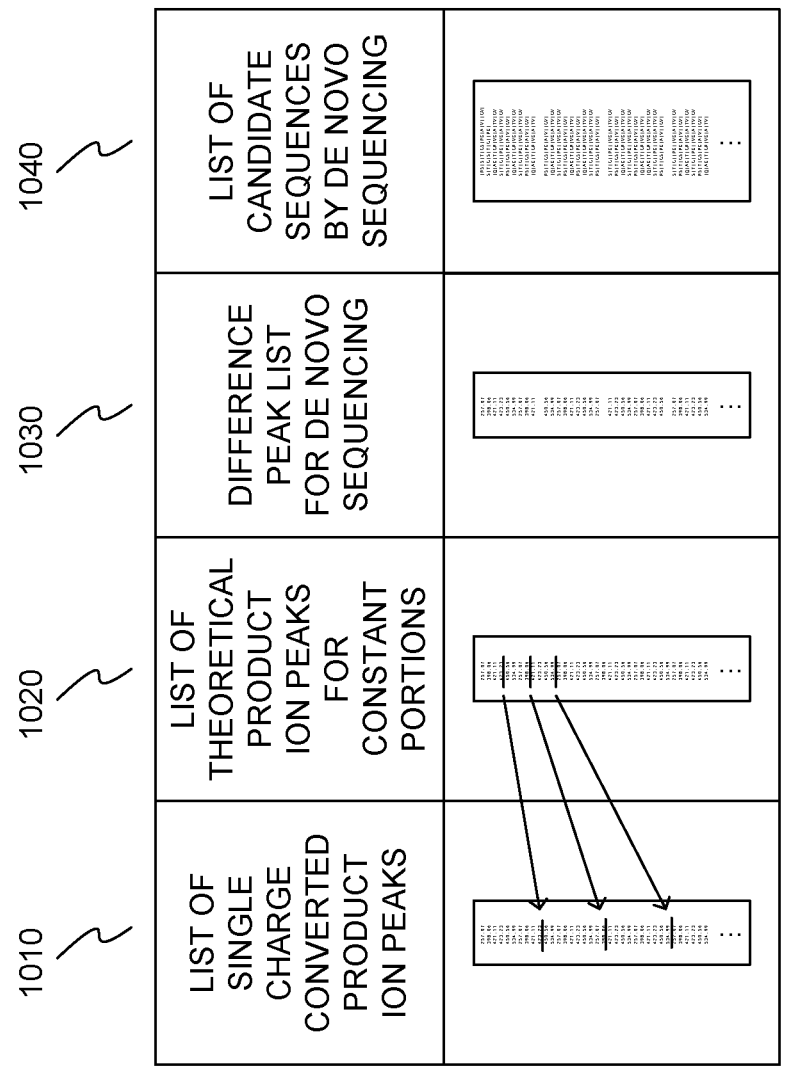
FIG. 10 is an exemplary table showing a difference product ion peak list produced by removing or subtracting theoretical product ion peaks for constant portions of an mAbs class from a calculated list of single charge converted product ion peaks and showing a list of de novo sequences that correspond to the difference product ion peak list, in accordance with various embodiments.

FIG. 10 is an exemplary table 1000 showing a difference product ion peak list produced by removing or subtracting theoretical product ion peaks for constant portions of an mAbs class from a calculated list of single charge converted product ion peaks and showing a list of de novo sequences that correspond to the difference product ion peak list, in accordance with various embodiments. In table 1000, the product ion peaks of list 1020 of theoretical product ion peaks for constant portions of the known mAb class are compared to the product ion peaks of list 1010 of singly charged products ions. Matching peaks are removed from list 1010, producing difference peak list 1030. De novo sequencing is applied to the product ion peaks of difference peak list 1030, producing list 1040 of de novo candidate sequences of the variable portion of the unknown mAbs.

Method for Sequencing Variable Portion of Unknown mAb

Figure 11:
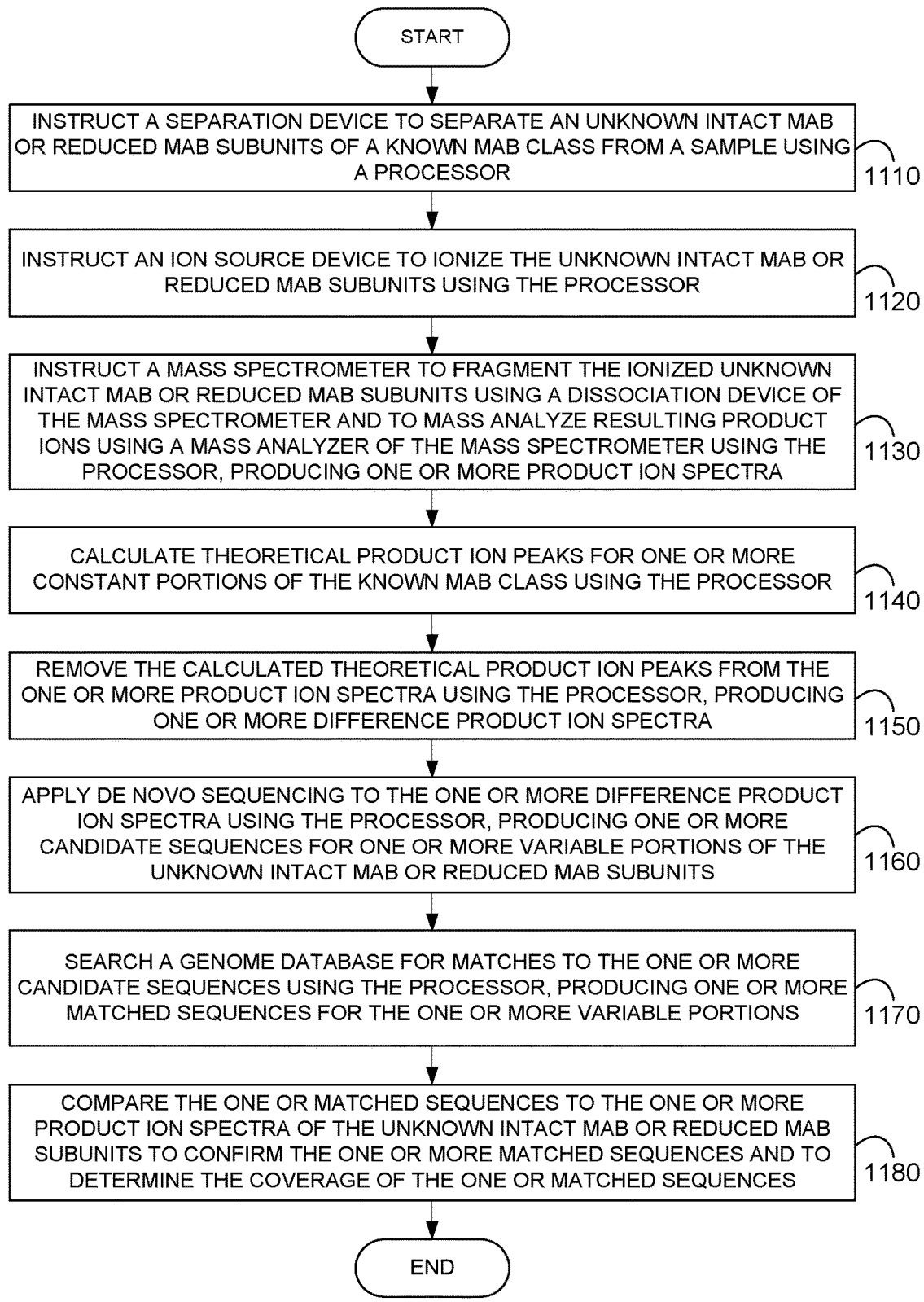
FIG. 11 is a flowchart showing a method for sequencing one or more variable portions of an unknown mAb, in accordance with various embodiments.

FIG. 11 is a flowchart showing a method 1100 for sequencing one or more variable portions of an unknown mAb, in accordance with various embodiments.

In step 1110 of method 1100, a separation device is instructed to separate an unknown intact mAb or reduced mAb subunits of a known mAb class from a sample using a processor.

In step 1120, an ion source device is instructed to ionize the unknown intact mAb or reduced mAb subunits using the processor.

In step 1130, a mass spectrometer is instructed to fragment the ionized unknown intact mAb or reduced mAb subunits using a dissociation device of the mass spectrometer and to mass analyze resulting product ions using a mass analyzer of the mass spectrometer using the processor, producing one or more product ion spectra.

In step 1140, theoretical product ion peaks are calculated for one or more constant portions of the known mAb class using the processor.

In step 1150, the calculated theoretical product ion peaks are removed from the one or more product ion spectra using the processor, producing one or more difference product ion spectra.

In step 1160, de novo sequencing is applied to the one or more difference product ion spectra using the processor, producing one or more candidate sequences for one or more variable portions of the unknown intact mAb or reduced mAb subunits.

In step 1170, a genome database is searched for matches to the one or more candidate sequences using the processor, producing one or more matched sequences for the one or more variable portions.

In various embodiments, in additional step 1180, the one or matched sequences are compared to the one or more product ion spectra of the unknown intact mAb or reduced mAb subunits to confirm the one or more matched sequences and to determine the coverage of the one or matched sequences. For example, step 1180 is performed to determine the 70-80% sequence coverage of one or more matched sequences 654 of FIG. 6.

Computer Program Product for Sequencing Variable Portion of Unknown mAb

In various embodiments, computer program products include a tangible computer-readable storage medium whose contents include a program with instructions being executed on a processor so as to perform a method for sequencing one or more variable portions of an unknown mAb. This method is performed by a system that includes one or more distinct software modules.

Figure 12:
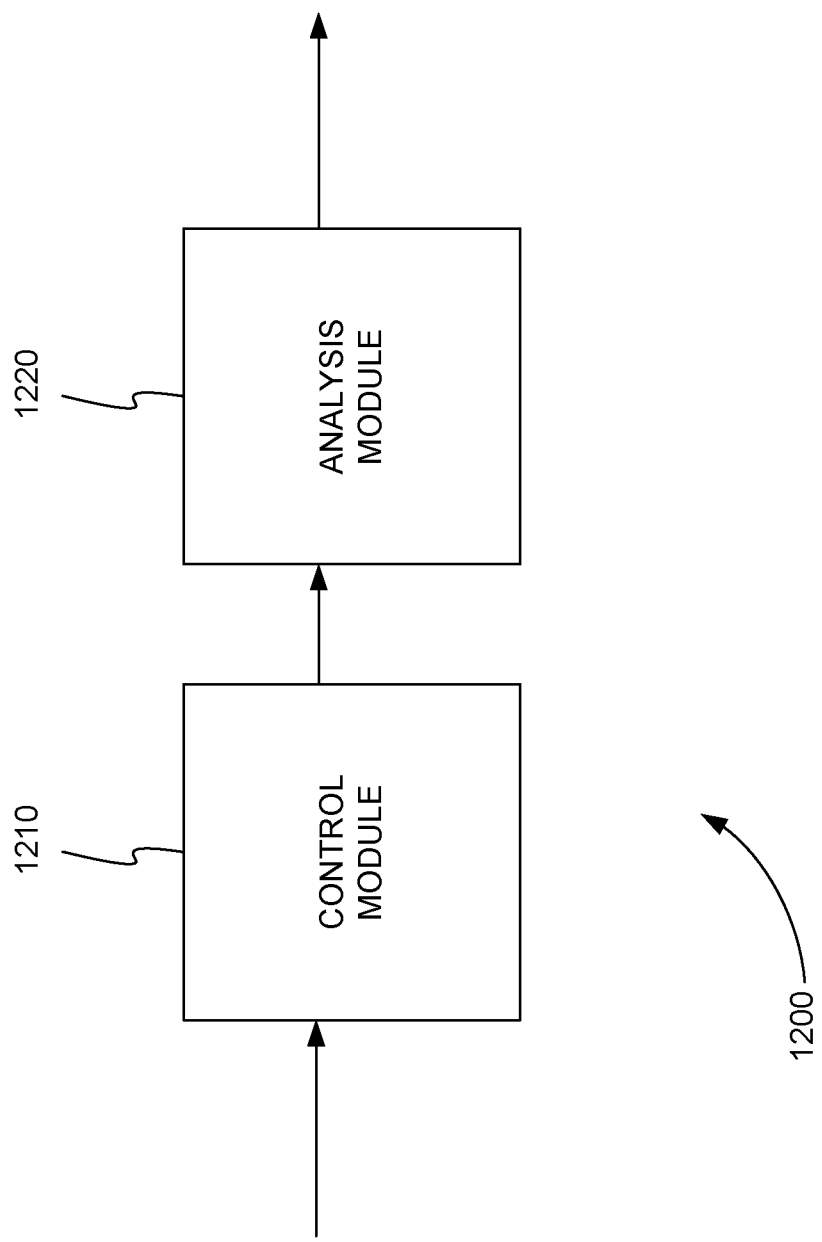
FIG. 12 is a schematic diagram of a system that includes one or more distinct software modules that perform a method for sequencing one or more variable portions of an unknown mAb, in accordance with various embodiments.

FIG. 12 is a schematic diagram of a system 1200 that includes one or more distinct software modules that perform a method for sequencing one or more variable portions of an unknown mAb, in accordance with various embodiments. System 1200 includes control module 1210 and analysis module 1220.

Control module 1210 instructs a separation device to separate an unknown intact mAb or reduced mAb subunits of a known mAb class from a sample. Control module 1210 instructs an ion source device to ionize the unknown intact mAb or reduced mAb subunits. Control module 1210 instructs a mass spectrometer to fragment the ionized unknown intact mAb or reduced mAb subunits using a dissociation device of the mass spectrometer. Control module 1210 also instructs the mass spectrometer to mass analyze resulting product ions using a mass analyzer of the mass spectrometer, producing one or more product ion spectra.

Analysis module 1220 calculates theoretical product ion peaks for one or more constant portions of the known mAb class. Analysis module 1220 removes the calculated theoretical product ion peaks from the one or more product ion spectra, producing one or more difference product ion spectra. Analysis module 1220 applies de novo sequencing to the one or more difference product ion spectra, producing one or more candidate sequences for one or more variable portions of the unknown intact mAb or reduced mAb subunits. Finally, analysis module 1220 searches a genome database for matches to the one or more candidate sequences, producing one or more matched sequences for the one or more variable portions.

In various embodiments, analysis module 1220 further compares the one or matched sequences to the one or more product ion spectra of the unknown intact mAb or reduced mAb subunits to confirm the one or more matched sequences and to determine the coverage of the one or matched sequences.

Experimental Data

ECD provides unique features, such as top-down sequencing, de novo sequencing, glycosylation analysis, and informative disulfide bond cleavage, and is an ideal tool to analyze intact antibodies. A small and high throughput ECD device based on an RF ion trap was used in a number of experiments. This technology was applied to an intact mAb in this work. It was also applied to a mAb subunits that were reduced using a novel online disulfide bond reduction technique.

The ECD cell was installed between Q1 and Q2 in a quadrupole-TOF system. A simultaneous trapping ECD mode was used for high throughput analysis, which is a simultaneous injection of the electron beam and precursor ions into the ECD device. Typical electron beam irradiation time was 10 ms, and the electron beam intensity was tuned to obtain appropriate dissociation efficiency. The mass resolution of the TOF was 35,000-47,000, which resolved isotope patterns of fragments up to Z~30+. A desalting LC column (Waters) was used for desalting, online reduction, and LC separation. Humanized monoclonal IgG (NIST-mAb) was obtained from NIST for demonstration purposes.

To obtain the best sequence coverage in top-down analysis using the ECD-TOF system, (1) a lower charged precursor may be selected to obtain lower fragment charge state distribution, (2) ECD may be performed with electron energy of 0-3eV, and (3) precursor consumption of 30~50% may be used to detect large fragments in highly charged states. Using a longer electron irradiation (or stronger electron beam) was found to induce secondary dissociation of primary ECD fragments, which removes the large fragments and produces internal fragments, which are not informative for sequencing.

Intact NIST-mAb was analyzed by the LC-ECD-TOF mass spectrometer. De novo sequencing on the intact ECD spectrum obtained by a single LC run indicated three sequences, and two of them were matched to N terminal partial sequences of the variable parts in a light chain and a heavy chain found in the human genome. The intact ECD spectrum was further analyzed in top-down manner using the suggested full sequences (the full sequence is provided by NIST), where the data covered the variable parts of the light chain and the heavy chain of the mAb. ECD at 3 eV did not cleave the disulfide-bonded rings in the protein.

To obtain nearly complete sequence coverage, IdeS enzyme (Genovis) was applied. For the online reduction of disulfide bonds, DTT was injected into the intact mAb and the IdeS digest trapped on the desalting column for 1 min. By applying the reduction, sequence coverages of 84.7% for the light chain, 78.3% for the variable part of the heavy chain (Fd'), and 84.7% for the fixed part of the heavy chain (scFc) were obtained. Further, ECD indicated the glycosylation site and its mass in scFc, and CID informed the glycan composition.

While the present teachings are described in conjunction with various embodiments, it is not intended that the present teachings be limited to such embodiments. On the contrary, the present teachings encompass various alternatives, modifications, and equivalents, as will be appreciated by those of skill in the art.

Further, in describing various embodiments, the specification may have presented a method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process should not be limited to the performance of their steps in the order written, and one skilled in the art can readily appreciate that the sequences may be varied and still remain within the spirit and scope of the various embodiments.

What is claimed is:

1. A system for sequencing one or more variable portions of an unknown monoclonal antibody (mAb), comprising:
   a genome database for homology search;
   a separation device,
   an ion source;
   a mass spectrometer that includes a dissociation device and a mass analyzer; and
   a processor that
     instructs the separation device to separate an unknown intact mAb or reduced mAb subunits of a known mAb class from a sample,
     instructs the ion source device to ionize the unknown intact mAb or reduced mAb subunits,
     instructs the mass spectrometer to fragment the ionized unknown intact mAb or reduced mAb subunits using the dissociation device and mass analyze resulting product ions using the mass analyzer, producing one or more product ion spectra,
     calculates theoretical product ion peaks for one or more constant portions of the known mAb class,
     removes the calculated theoretical product ion peaks from the one or more product ion spectra, producing one or more difference product ion spectra,
     applies de novo sequencing to the one or more difference product ion spectra, producing one or more candidate sequences for one or more variable portions of the unknown intact mAb or reduced mAb subunits, and
     searches the genome database for matches to the one or more candidate sequences, producing one or more matched sequences for the one or more variable portions.

2. The system of claim 1, wherein the processor removes the calculated theoretical product ion peaks by removing theoretical product ion peaks of N terminal product ions.

3. The system of claim 2, wherein the processor applies de novo sequencing to remaining C product ions of the one or more difference product ion spectra to produce one or more candidate sequences.

4. The system of claim 1, wherein the processor calculates a peak list from the one or more product ion spectra.

5. The system of claim 4, wherein the processor calculates a peak list from the one or more product ion spectra that are converted to singly charged product ion peaks.

6. The system of claim 4, wherein the processor removes the calculated theoretical product ion peaks from the one or more product ion spectra by removing the theoretical product ion peaks from the peak list, producing a difference peak list.

7. The system of claim 6, wherein the processor applies de novo sequencing to the one or more difference product ion spectra by applying de novo sequencing to the difference peak list.

8. The system of claim 1, further comprising applying immunoglobulin G-degrading enzyme of Streptococcus pyogenes (IdeS) digestion to the intact unknown mAb to produce the reduced unknown mAb before the processor instructs the separation device to separate and desalt the reduced unknown mAb.

9. The system of claim 8, further comprising injecting dithiothreitol (DTT) into solution with the intact unknown mAb and into the separation device as the separation device is separating and desalting the IdeS digested reduced unknown mAb.

10. The system of claim 1, wherein the dissociation device comprises an electron capture dissociation (ECD) device.

11. The system of claim 10, wherein the processor instructs the mass spectrometer to use an electron energy between 0 and 3 eV to fragment the ionized unknown intact mAb or reduced mAb subunits using the ECD device.

12. The system of claim 10, wherein the mass spectrometer simultaneously injects electrons and ions of the unknown intact mAb or reduced mAb subunits into the ECD device.

13. The apparatus of claim 10, wherein the ECD device comprises a quadrupole, hexapole, or octupole dissociation device.

14. A method for sequencing one or more variable portions of an unknown monoclonal antibody (mAb), comprising:
   instructing a separation device to separate an unknown intact mAb or reduced mAb subunits of a known mAb class from a sample using a processor;
   instructing an ion source device to ionize the unknown intact mAb or reduced mAb subunits using the processor;
   instructing a mass spectrometer to fragment the ionized unknown intact mAb or reduced mAb subunits using a dissociation device of the mass spectrometer and to mass analyze resulting product ions using a mass analyzer of the mass spectrometer using the processor, producing one or more product ion spectra;
   calculating theoretical product ion peaks for one or more constant portions of the known mAb class using the processor;
   removing the calculated theoretical product ion peaks from the one or more product ion spectra using the processor, producing one or more difference product ion spectra;
   applying de novo sequencing to the one or more difference product ion spectra using the processor, producing one or more candidate sequences for one or more variable portions of the unknown intact mAb or reduced mAb subunits; and searching a genome database for matches to the one or more candidate sequences using the processor, producing one or more matched sequences for the one or more variable portions.

15. A computer program product, comprising a non-transitory and tangible computer-readable storage medium whose contents include a program with instructions being executed on a processor so as to perform a method for sequencing one or more variable portions of an unknown monoclonal antibody (mAb), the method comprising:

providing a system, wherein the system comprises one or more distinct software modules, and wherein the distinct software modules comprise a control module and an analysis module;

instructing a separation device to separate an unknown intact mAb or reduced mAb subunits of a known mAb class from a sample using the control module;

instructing an ion source device to ionize the unknown intact mAb or reduced mAb subunits using the control module;

instructing a mass spectrometer to fragment the ionized unknown intact mAb or reduced mAb subunits using a dissociation device of the mass spectrometer and to mass analyze resulting product ions using a mass analyzer of the mass spectrometer using the control module, producing one or more product ion spectra;

calculating theoretical product ion peaks for one or more constant portions of the known mAb class using the analysis module;

removing the calculated theoretical product ion peaks from the one or more product ion spectra using the analysis module, producing one or more difference product ion spectra;

applying de novo sequencing to the one or more difference product ion spectra using the analysis module, producing one or more candidate sequences for one or more variable portions of the unknown intact mAb or reduced mAb subunits; and searching a genome database for matches to the one or more candidate sequences using the analysis module, producing one or more matched sequences for the one or more variable portions.

* * * * *